United States Patent [19]
Diercks et al.

[11] Patent Number: 5,854,163
[45] Date of Patent: Dec. 29, 1998

[54] PROCESS FOR PREPARING PHOSPHORUS-DOPED SILVER CATALYSTS

[75] Inventors: Rainer Diercks; Günther Schönaich, both of Neuhofen, Germany

[73] Assignee: BASF Aktiengesellschaft, Ludwigshafen, Germany

[21] Appl. No.: 913,106

[22] PCT Filed: Mar. 4, 1996

[86] PCT No.: PCT/EP96/00901

§ 371 Date: Sep. 15, 1997

§ 102(e) Date: Sep. 15, 1997

[87] PCT Pub. No.: WO96/28249

PCT Pub. Date: Sep. 19, 1997

[30] Foreign Application Priority Data

Mar. 15, 1995 [DE] Germany .............. 195 09 359.3

[51] Int. Cl.$^6$ .............. C01J 20/34; C01J 38/02; C01J 27/14; C01J 23/50
[52] U.S. Cl. .............. 502/56; 502/208; 502/347
[58] Field of Search .............. 502/56, 208, 347

[56] References Cited

U.S. PATENT DOCUMENTS 4,235,823  11/1980  Dudeck et al. .............. 568/402

FOREIGN PATENT DOCUMENTS 0104666  4/1984  European Pat. Off. ........ C07C 47/04

*Primary Examiner*—Michael L. Lewis
*Assistant Examiner*—Alexander G. Ghyka
*Attorney, Agent, or Firm*—Oblon, Spivak, McClelland, Maier & Neustadt, P.C.

[57] ABSTRACT

A process for preparing phosphorus-doped silver catalysts from silver contaminated with phosphorus compounds, which comprises a) heating the silver which is contaminated with phosphorus compounds to temperatures at which the silver is liquid and subsequently cooling to temperatures below the melting point, b) preparing silver crystals from the silver obtained in stage a) by anodically oxidizing it to silver ions in an electrolysis cell with an aqueous electrolyte, and cathodically reducing the silver ions again to elemental silver, and c) contacting the silver crystals with a finely divided phosphorus compound with a melting point or decomposition temperature above 500° C. (phosphorus compound P).

10 Claims, No Drawings

PROCESS FOR PREPARING PHOSPHORUS-DOPED SILVER CATALYSTS

BACKGROUND OF THE INVENTION

1. Field of the Invention

The present invention relates to a process for preparing phosphorus-doped silver catalysts from silver contaminated with phosphorus compounds.

2. Description of the Background

Processes for preparing silver catalysts suitable for oxidizing methanol to formaldehyde are generally known (cf. Ullmann's Enzyklopädie der technischen Chemie, 3rd Edition, Urban und Schwarzenberg, Munich-Berlin, 1956, Volume 7, pages 660 to 663). In this process, silver is anodically oxidized in an electrolytic cell to silver ions, and cathodically reduced again to silver. An aqueous solution of silver nitrate and nitric acid is recommended as electrolyte. The coarsely crystalline silver formed at the cathode is suitable as catalyst for synthesizing formaldehyde from methanol.

According to DE-A 1166171, particularly high yields can be obtained in the oxidation of methanol to formaldehyde on use of a silver catalyst prepared by the following process: silver which has, where appropriate, initially been heated at 500° to 600° C. in a stream of oxygen-containing gases is subjected to electrolysis at least twice, with the current density in the first electrolysis or the initial electrolyses being above 250, in particular from 300 to 500, $A/m^2$ of cathode area and in the last electrolysis being below 250, in particular from 100 to 200, $A/m^2$ of cathode area.

EP-A 0104666 discloses that the selectivity in the preparation of formaldehyde from methanol using a silver catalyst can be increased by using small amounts of phosphorus compounds as promoters in addition to the silver catalyst.

Advantageous effects occurring on use of phosphorus compounds as promoters for the oxidation of methanol to formaldehyde in the presence of a silver catalyst are furthermore disclosed in CN-A 85100530, EP-A 0467169 and JP-A 38227/83.

EP-A 0467169 describes the preparation of a fixed bed catalyst which is composed of layers of silver crystals which contain a phosphorus-containing salt in powder form as promoter. Particularly high yields and conversions can be obtained in the preparation of formaldehyde from methanol using this phosphorus-doped fixed bed silver catalyst.

The commercial use of the processes for preparing formaldehyde using phosphorus compounds as promoters has hitherto been impeded by the fact that no economic processes are known for regenerating the used silver catalysts which result in these processes and which are contaminated with phosphorus compounds. A process for regenerating these catalysts is important for the economics of the preparation of formaldehyde because the catalysts have lost so much activity after about 8 weeks of use that the space-time yield is unsatisfactory.

Regeneration of silver catalysts contaminated with phosphorus compounds by one of the previously described processes for preparing silver catalysts results in silver catalysts which have little suitability for economic preparation of formaldehyde on the industrial scale for the following reasons:

When a silver catalyst used in a conventional continuously operated plant for the industrial production of formaldehyde loses its activity, it is necessary to stop the production process in order to be able to remove the catalyst from the plant and replace it by a regenerated catalyst with higher activity. When the synthetic process is started up again, it is necessary to preheat the stream of gaseous starting materials which is passed over the catalyst. Temperatures of about 300° to 350° C. are necessary for this in the case of regenerated catalysts which have been used without phosphorus compounds as promoters. Once the reaction has started, it is unnecessary for the stream of gas to be preheated further because the reaction zone (catalyst) heats up to about 700° C. because of the heat liberated in the reaction for the formaldehyde synthesis.

On use of regenerated silver catalysts which have been used together with phosphorus compounds as promoters, it is necessary for the stream of gaseous starting materials to be preheated to at least 700° C. for the reaction to start up.

The preheating of the stream of gas to such a high temperature is very costly industrially. The equipment necessary for this is not available in the plants normally used for industrial production of formaldehyde.

Gmelins Handbuch der anorganischen Chemie, Verlag Chemie GmbH 1970, 8th Edition, Part A2, System Number 61, pages 34 to 35, discloses the preparation of pure silver by concentrating crude silver by a melt process (cupellation) as far as possible and subsequently further purifying the silver by electrolysis. In this case, the silver is dissolved anodically and deposited cathodically in a solution of silver nitrate in nitric acid.

The cupellation in which crude silver is heated in the presence of air at from 900° to 1100° C. (cf. loc. cit. pages 7 to 9) is, however, recommended only for crude silver which is contaminated with Pb, Cu, As, Sb, Zn, Se and Te.

SUMMARY OF THE INVENTION

It is an object of the present invention to provide a process for preparing phosphorus-doped silver catalysts which does not have the prior art disadvantages.

We have found that this object is achieved by a process which comprises a) heating the silver which is contaminated with phosphorus compounds to temperatures at which the silver is liquid and subsequently cooling to temperatures below the melting point, b) preparing silver crystals from the silver obtained in stage a) by anodically oxidizing it to silver ions in an electrolysis cell with an aqueous electrolyte, and cathodically reducing the silver ions again to elemental silver, and c) contacting the silver crystals with a finely divided phosphorus compound with a melting point or decomposition temperature above 500° C. (phosphorus compound P).

DETAILED DESCRIPTION OF THE INVENTION

A particularly suitable starting material for the process according to the invention is silver which contains about 0.01 to 1000 ppm, preferably 1 to 100 ppm, phosphorus or phosphorus compounds, calculated as elemental phosphorus, but is virtually free of impurities such as Pb, Cu, As, Sb, Zn, Se, Te and noble metals. Silver contaminated in this way results, for example, when silver is used as catalyst together with phosphorus-containing promoters for oxidizing methanol to formaldehyde. Processes which result in catalysts which are contaminated in this way and require regeneration are disclosed, for example, in EP-A 0104666, CN-A 85100530 and JP-A 38227/83.

The catalysts used in these processes are obtained, for example, by silver being impregnated with solutions of phosphorus or organic phosphorus compounds, eg. triphenylphosphine, or inorganic phosphorus compounds, eg. orthophosphoric acid, or exposed to phosphorus vapor.

The phosphorus-contaminated silver which is particularly preferably employed is a used phosphorus-doped silver catalyst as results from the preparation of formaldehyde by oxidative dehydrogenation of methanol by the process described in EP-A 0467169.

In this process, an initial phosphorus-doped silver catalyst which is obtainable by contacting silver crystals which are virtually free of phosphorus compounds and other impurities with a phosphorus-containing salt, eg. phosphates or polyphosphates of alkali metals or alkaline earth metals, by a generally known process (cf. Ullmann's Enzyklopädie der technischen Chemie, 3rd Edition, Urban und Schwarzenberg, Munich-Berlin, 1956, Volume 7, pages 660 to 661) is used for the oxidative dehydrogenation of methanol to formaldehyde.

The melting of the silver in step (a) of the process according to the invention preferably takes place in the presence of from 1 to 100% by weight, based on the silver, of a compound or of a mixture of compounds selected from a group of alkaline earth metal oxides, preferably calcium oxide, silicon dioxide or aluminum oxide.

Particularly suitable for this purpose are ternary and binary mixtures of silicon dioxide, aluminum oxide and calcium oxide, which are particularly preferably used as eutectic mixtures in order to keep the melting point as low as possible.

The silver is generally heated in the presence of oxygen for from 0.5 to 10 min at temperatures at which the silver is liquid under normal conditions, preferably at from 960.8 to 1500° C. If the silver is melted in the presence of additives, the temperature is beneficially above the melting point of these additives.

The silver is then cooled. It is advantageous to do this by pouring the molten silver into water in order to remove any water-soluble impurities.

In the next step (b), the silver is subjected to electrolysis. In this, the silver is anodically oxidized to silver ions in an electrolysis cell with an aqueous electrolyte, and is cathodically reduced again to elemental silver. Processes suitable for this purpose are those generally known for the purification of silver by electrolysis (cf. Hollemann-Wiberg, Lehrbuch der anorganischen Chemie, 91st–100th Editions, Verlag Walter de Gruyter 1985, pages 1012–1013).

Elemental silver in the form of silver crystals which are particularly suitable as catalysts for formaldehyde synthesis are obtained, in particular, when the electrolysis is carried out by the process described in German Patent 1166171.

An aqueous silver nitrate solution is preferably employed as electrolyte. This silver nitrate solution generally has a pH of from 1 to 4 and contains from 1 to 5% by weight of silver. The pH is beneficially adjusted with nitric acid.

The electrodes used as those normally employed in the electrolysis of silver. Suitable anodes are bags into which the silver to be oxidized has generally been introduced as granules or powder. Silver plates are particularly suitable cathodes.

The electrolysis is beneficially carried out at current densities of from 80 to 500 A/m$^2$ of cathode area and electrolyte temperatures of from 10 to 30° C.

In order to reach these current densities, voltages of from 1 to 15 volts are necessary in most electrolysis cells.

It is advisable continuously to remove the silver crystals from the cathode as they are formed. Silver crystals with a size of from 0.2 to 5 mm are generally obtained.

In most cases a single electrolysis is sufficient to obtain usable silver crystals.

The silver crystals are contacted in step (c) with a finely divided phosphorus compound with a melting point or decomposition temperature above 500° C. (phosphorus compound P). Phosphorus-containing salts in powder form which have a melting point or decomposition temperature above 800° C. are preferred.

Examples of suitable salts are inorganic phosphates of alkali metals and alkaline earth metals, heavy metals, eg. Ag, Zn and Fe or of boron and ammonium.

Phosphates or pyrophosphates of alkali metals or alkaline earth metals, eg. $Na_4P_2O_7$, $Li_3PO_4$, $Mg_3(PO_4)_2$, $Ca_3(PO_4)_2$, are preferred.

The particle size of the compounds (P) is not critical and is, in general, from about 1 mm to 1 µm.

The phosphorus-doped silver catalyst preferably contains from 0.1 to 0.0001 g, particularly preferably from 0.01 to 0.001 g, of compound (P), calculated as elemental phosphorus, per cm$^3$ of silver crystals.

The general procedure for preparing the phosphorus-doped silver catalysts from the silver crystals is as described in EP-A 0467169. In this process, the silver crystals are arranged to give a fixed bed catalyst which consists of several layers of the silver crystals, as disclosed, for example, in DE-A 2322757, and compound (P) in the form of a powder is applied to one or more of these layers, resulting in a phosphorus-doped fixed bed silver catalyst.

In general, a phosphorus-doped fixed bed silver catalyst consists of from 4 to 9 layers of silver crystals and has a total layer thickness of from 5 to 50 mm.

The amount of phosphorus compound (P), calculated as elemental phosphorus, is generally from 0.1 to 100 mg, preferably 0.5 to 50 mg, per cm$^2$ of cross-sectional area of the phosphorus-doped fixed bed silver catalyst.

A phosphorus-doped fixed bed silver catalyst can be prepared particularly simply by installing a fixed bed catalyst consisting of the silver crystals in a tubular reactor in such a way that the layers are arranged perpendicular to the direction of flow of a gas which is passed through the tubular reactor, and by subsequently distributing the compound (P) on the topmost layer of silver crystals. It is expedient for the cross-sectional areas of the tubular reactor and of the phosphorus-doped fixed bed silver catalyst to be approximately the same.

These tubular reactors equipped with a phosphorus-doped fixed bed silver catalyst are suitable for preparing formaldehyde by oxidative dehydrogenation of methanol by passing methanol and oxygen through the tubular reactor at a temperature of, normally, from 500° to 750° C. This process is disclosed, for example, in Ullmann's Enzyklopädie der technischen Chemie, 3rd Edition, Urban und Schwarzenberg, Munich-Berlin, 1956, Volume 7, pages 660 to 661, or in EP-A 0467169.

The phosphorus-doped silver catalysts prepared in this way are particularly distinguished by it being sufficient to preheat the reactants in the presence of the catalysts to relatively low temperatures in order to start the formaldehyde preparation process, with which formaldehyde can be prepared with high conversion and high selectivity.

EXAMPLES

A. Preparation of the phosphorus-doped silver catalysts

Example 1

A silver catalyst which had been prepared according to the example with the experiment no. 3 from EP-A 0467169 (charged with $Na_4P_2O_7$) was operated for 2000 hours to synthesize formaldehyde.

For workup, 50 g of the catalyst were initially washed with distilled water for 1 h. The content of phosphorus compounds was, measured as elemental phosphorus, 27 ppm.

The catalyst was heated at 1200° C. for 15 min and then poured into distilled water, after which the content of phosphorus compounds was less than 1 ppm (detection limit).

A new silver catalyst was then prepared from the silver by the Möbius electrolytic process (cf. Ullmann's Enzyklopädie der technischen Chemie, 3rd Edition, Urban und Schwarzenberg, Munich-Berlin, 1956, Volume 7, pages 660 to 661). Electrolysis conditions: current density 120 $A/m^2$; electrolyte temperature 27° C.; aqueous silver nitrate solution with a pH of 2.5 and a silver concentration of 3 g/l.

Example 2

The silver catalyst was prepared as described in Example 1, but the used catalyst was melted in the presence of 25% by weight, based on the catalyst, of a mixture of aluminum oxide and calcium oxide in the ratio 1:1 by weight.

Comparative Example

The silver catalyst was prepared as in the example in German Patent 1166171.

B. Properties of the silver catalysts

The silver catalysts which had been prepared as in Examples 1 and 2 and the comparative example were used as described in the example in EP-A 0467169, together with $Na_4P_2O_7$ as promoter, in the experimental reactor described therein. The experimental conditions were otherwise chosen as in experiment no. 3. It was possible to reproduce the result of experiment no. 3 with the catalysts of Examples 1 and 2. The reaction started when the starting materials were at 330° C.

When the catalyst from the comparative example was used, the reaction did not start despite heating the starting materials to 550° C.

We claim:

1. A process for preparing phosphorus-doped silver catalysts from silver contaminated with phosphorus compounds, which comprises a) heating said silver which is contaminated with phosphorus compounds to temperatures at which said silver is liquid and subsequently cooling to temperatures below the melting point, b) preparing silver crystals from the silver obtained in stage a) by anodically oxidizing it to silver ions in an electrolysis cell with an aqueous electrolyte, and cathodically reducing the silver ions again to elemental silver, and c) contacting the silver crystals with a finely divided phosphorus compound (P), wherein said compound (P) has a melting point or decomposition temperature above 500° C.

2. A process as claimed in claim 1, wherein the silver contaminated with phosphorus compounds is heated in the presence of from 1 to 100% by weight, based on the silver, of a compound or of a mixture of compounds selected from the group consisting of alkaline earth metal oxides, silicon dioxide and aluminum oxide, to temperatures above the melting point of these compounds or of the corresponding mixtures.

3. A process as claimed in claim 1, wherein the liquid silver is cooled by pouring into deionized water.

4. A process as claimed in claim 1, wherein an aqueous silver nitrate solution is used as electrolyte.

5. A process as claimed in claim 1, wherein the current density in the electrolysis is from 80 to 500 $A/m^2$ of electrode area.

6. A process as claimed in claim 1, wherein an alkali metal or alkaline earth metal phosphate or an alkali metal or alkaline earth metal pyrophosphate is used as compound (P).

7. A process as claimed in claim 1, wherein a used phosphorus-doped silver catalyst which is obtainable by using an initial phosphorus-doped silver catalyst for the oxidative dehydrogenation of methanol to formaldehyde is employed as phosphorus-contaminated silver.

8. A process as claimed in claim 1, wherein a phosphorus-doped fixed bed silver catalyst is prepared by arranging the silver crystals to give a fixed bed silver catalyst which consists of one or more layers of silver crystals, and distributing the phosphorus compound (P) on one or more of these layers.

9. A process as claimed in claim 8, wherein the silver crystals are arranged to give a fixed bed silver catalyst consisting of from 4 to 9 layers.

10. A process as claimed in claim 8, wherein the silver crystals are arranged to give a fixed bed silver catalyst with a total layer thickness of from 5 to 50 mm.

* * * * *

UNITED STATES PATENT AND TRADEMARK OFFICE
CERTIFICATE OF CORRECTION

PATENT NO. : 5,854,163
DATED : December 29, 1998
INVENTOR(S) : Rainer DIERCKS et al.

It is certified that error appears in the above-identified patent and that said Letters Patent is hereby corrected as shown below:

On the title page, item [87], PCT Pub. Date should be:

--Sep. 19, 1996--

Signed and Sealed this

Sixth Day of July, 1999

Q. TODD DICKINSON

*Attest:*

*Attesting Officer*  Acting Commissioner of Patents and Trademarks